United States Patent
Kondo

(10) Patent No.: US 12,367,180 B2
(45) Date of Patent: Jul. 22, 2025

(54) IMAGE FORMING APPARATUS CAPABLE OF REDUCING LABOR REQUIRED WHEN PROVIDING IMAGE FILE, METHOD OF CONTROLLING IMAGE FORMING APPARATUS, AND STORAGE MEDIUM

(71) Applicant: CANON KABUSHIKI KAISHA, Tokyo (JP)

(72) Inventor: Yuichi Kondo, Chiba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 122 days.

(21) Appl. No.: 18/187,184

(22) Filed: Mar. 21, 2023

(65) Prior Publication Data

US 2023/0306001 A1    Sep. 28, 2023

(30) Foreign Application Priority Data

Mar. 24, 2022   (JP) .................. 2022-048669

(51) Int. Cl.
  *G06F 16/176*    (2019.01)
  *G06F 16/16*    (2019.01)
  (Continued)

(52) U.S. Cl.
  CPC .......... *G06F 16/176* (2019.01); *G06F 16/164* (2019.01); *G06F 16/166* (2019.01); *H04N 1/00244* (2013.01); *H04N 1/00427* (2013.01)

(58) Field of Classification Search
  CPC .... G06F 16/176; G06F 16/164; G06F 16/166; H04N 1/00244; H04N 1/00427; G16H 10/60; G16H 30/20; G16H 40/67
  See application file for complete search history.

(56) References Cited

U.S. PATENT DOCUMENTS

| 9,648,200 B2 | 5/2017 | Mori et al. |
| 2002/0080392 A1* | 6/2002 | Parvulescu ............ G16H 30/40 358/1.15 |

(Continued)

FOREIGN PATENT DOCUMENTS

| JP | 2007013887 A | 1/2007 |
| JP | 2011181112 A | 9/2011 |
| JP | 2014192621 A | 10/2014 |

*Primary Examiner* — Robert W Beausoliel, Jr.
*Assistant Examiner* — Mohammad S Bhuyan
(74) *Attorney, Agent, or Firm* — ROSSI, KIMMS & McDOWELL LLP

(57) ABSTRACT

An image forming apparatus that communicates with a predetermined management system managing image files and a server storing image files to be provided to management systems including the predetermined management system. A reading section reads an original to generate an image of the original. A user selects information concerning file names of the image files. A controller converts the image of the original to an image file of a predetermined data format. A file name of the image file is set to a file name at least including the information selected by the user. The image file having the set file name is transmitted to the server. The controller identifies a collaborating one of the management systems, acquires a file name rule of the identified collaborating management system, and sets the file name of the image file according to the acquired file name rule.

7 Claims, 20 Drawing Sheets

(51) Int. Cl.
*G16H 10/60* (2018.01)
*G16H 30/20* (2018.01)
*G16H 40/67* (2018.01)
*H04N 1/00* (2006.01)

(56) References Cited

U.S. PATENT DOCUMENTS

| | | | |
|---|---|---|---|
| 2006/0285753 A1* | 12/2006 | Yamasaki | G16H 30/20 |
| | | | 382/209 |
| 2007/0250544 A1* | 10/2007 | Shibata | G06F 16/164 |
| 2008/0030800 A1* | 2/2008 | Matsukawa | H04N 1/00244 |
| | | | 358/474 |
| 2010/0003010 A1* | 1/2010 | Kim | H04N 5/772 |
| | | | 386/E5.002 |
| 2017/0060851 A1* | 3/2017 | Lai | G06V 30/40 |
| 2023/0214357 A1* | 7/2023 | Ghosh | G06F 16/164 |
| | | | 707/825 |

\* cited by examiner

FIG. 5A

| PATIENT NUMBER | PATIENT NAME | MEDICAL DPT. WHERE MEDICAL EXAMINATION IS RECEIVED | ADDRESS | CONTACT INFORMATION | ... |
|---|---|---|---|---|---|
| 1122 | KANJA TARO | SURGICAL DPT. | | | |
| 2233 | YAMADA HANAKO | OBSTETRICS & GYNECOLOGY DPT. | | | |
| 3344 | TANAKA KOZO | INTERNAL DPT. | | | |
| 4455 | SUZUKI SATOMI | PEDIATRICS DPT. | | | |
| 5566 | SATO KEISUKE | DERMATOLOGY DPT. | | | |
| 6677 | YOSHIDA KAORI | OBSTETRICS & GYNECOLOGY DPT. | | | |

| PATIENT NUMBER | PATIENT NAME | COLLABORATING MEDICAL INSTITUTION | ELECTRONIC MEDICAL CHART SYSTEM A | ELECTRONIC MEDICAL CHART SYSTEM B | ELECTRONIC MEDICAL CHART SYSTEM C OF THIS HOSPITAL |
|---|---|---|---|---|---|
| 1122 | KANJA TARO | ○○-CITY GENERAL HOSPITAL | ○ | | ○ |
| 2233 | YAMADA HANAKO | ○○-UNIVERSITY HOSPITAL | | ○ | ○ |
| 3344 | TANAKA KOZO | NONE | | | |

| ELECTRONIC MEDICAL CHART SYSTEM | FILE NAME RULE |
|---|---|
| A | PATIENT NUMBER_CLASSIFICATION_MEDICAL DEPT._DATE.pdf |
| B | PATIENT NUMBER_MEDICAL EXAMINATION DATE_CLASSIFICATION_ORDER NO._MEDICAL DEPT._DATE.pdf |
| C | PATIENT NUMBER_CLASSIFCATION_DATE.pdf |

Do you transmit the following document?

| Patient | 1122 Kanja Taro |
| --- | --- |
| Classification | Letter of introduction |
| Collaborating medical institution | ○○-city general hospital |

| Yes | No |

FIG. 9B

Reading in progress.

| Patient | 1122 Kanja Taro |
| --- | --- |
| Classification | Letter of introduction |

| Abort | Close |

FIG. 9C

Transmission in progress.

| File name | 1122_letter of introduction_20211225.pdf |
|---|---|
| Number of pages to be transmitted | 1 |

| Abort | Close |
|---|---|

FIG. 9D

Reading in progress.

| Patient | 1122 Kanja Taro |
|---|---|
| Classification | Letter of introduction |
| Collaborating medical institution | ○○-city general hospital |

| Abort | Close |
|---|---|

FIG. 9E

| Transmission in progress | |
|---|---|
| File name | 1122_letter of introduction_surgical dept._20211225.pdf |
| Number of pages to be transmitted | 1 |
| Collaborating medical institution | ○○-city general hospital |

| Abort | Close |

FIG. 12

| MEDICAL DEPT. | COLLABORATING MEDICAL INSTITUTION | ELECTRONIC MEDICAL CHART SYSTEM A | ELECTRONIC MEDICAL CHART SYSTEM B | ELECTRONIC MEDICAL CHART SYSTEM C OF THIS HOSPITAL |
|---|---|---|---|---|
| SURGICAL DEPT. | ○○-CITY GENERAL HOSPITAL | ○ | | ○ |
| OBSTETRICS & GYNECOLOGY DPT. | ○○-UNIVERSITY HOSPITAL | | ○ | ○ |
| INTERNAL DEPT. | NONE | | | |

1201

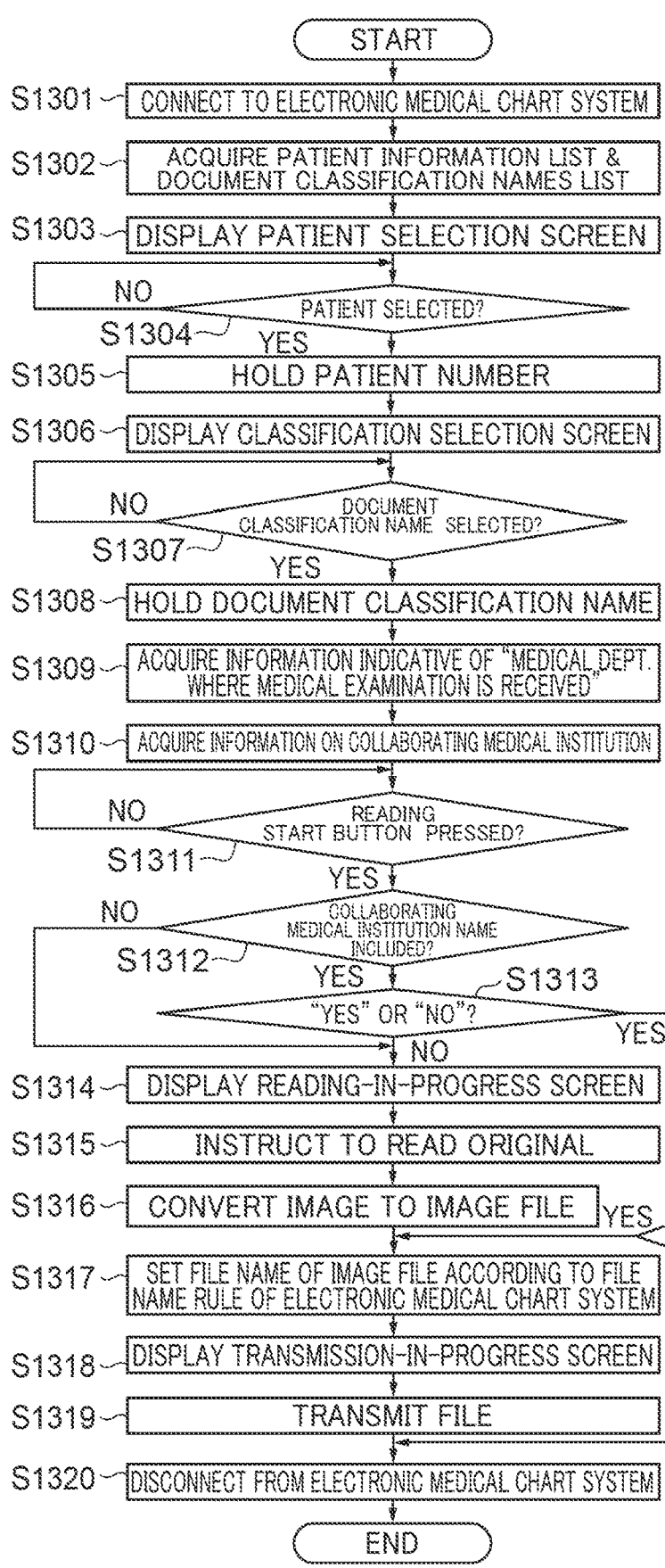
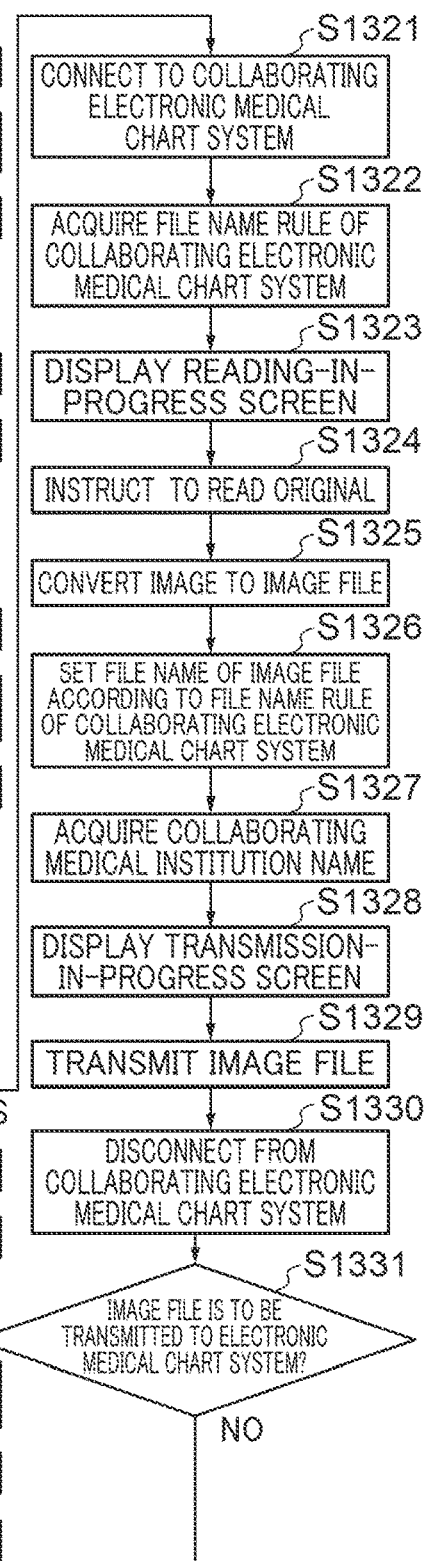
FIG. 13

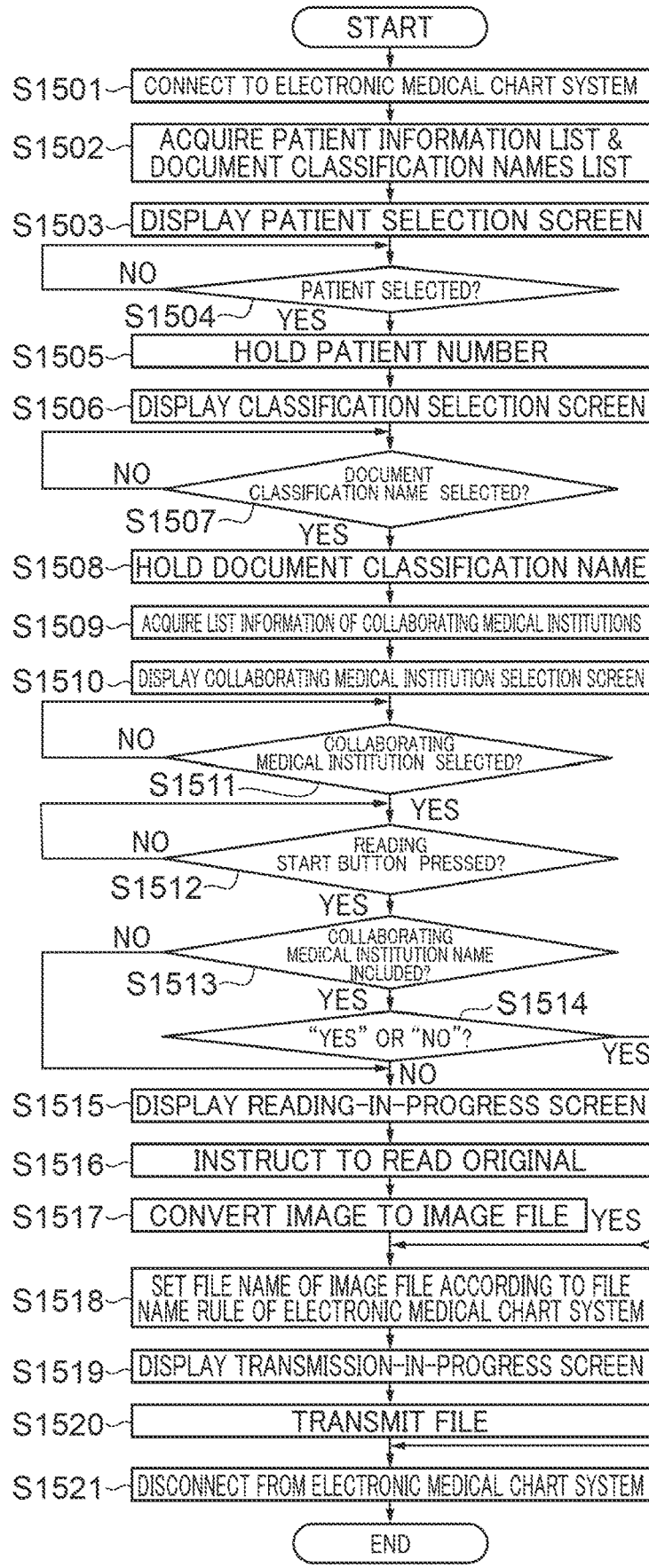
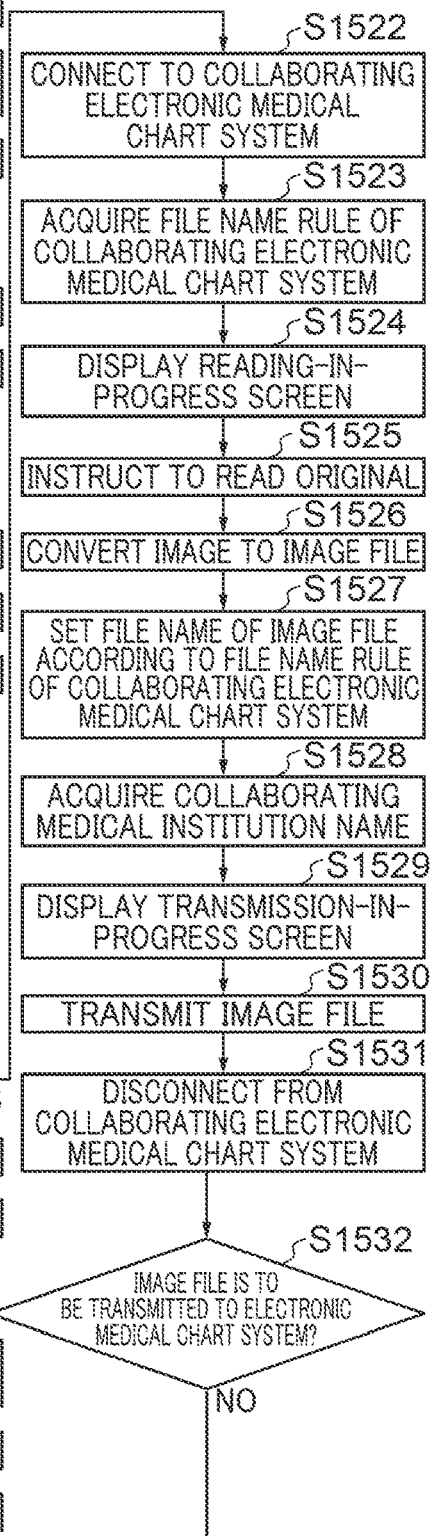
FIG. 15

IMAGE FORMING APPARATUS CAPABLE OF REDUCING LABOR REQUIRED WHEN PROVIDING IMAGE FILE, METHOD OF CONTROLLING IMAGE FORMING APPARATUS, AND STORAGE MEDIUM

FIELD OF THE INVENTION

The present invention relates to an image forming apparatus that is capable of reducing labor required when providing an image file, a method of controlling the image forming apparatus, and a storage medium.

DESCRIPTION OF THE RELATED ART

There is known a management system for managing image data. As an example of the management system, there is an electronic medical chart system that registers image data related to a patient in association with the patient and makes the registered image data referrable. In the electronic medical chart system, an image file is registered which is generated by converting a document, such as an interview sheet or a letter of introduction from another hospital, which is submitted from a patient for receiving a medical examination, to electronic data. When generating the above-mentioned image file of a document, an image forming apparatus equipped with a scanner function is used. The file name of the image file is set according to a file name rule set in advance (see e.g. Japanese Laid-Open Patent Publication (Kokai) No. 2007-13887, Japanese Laid-Open Patent Publication (Kokai) No. 2011-181112, and Japanese Laid-Open Patent Publication (Kokai) No. 2014-192621). For example, a file name formed by a patient number for identifying a patient, a classification name of a document, and so forth is set as the file name of the image file. When registering image files, the electronic medical chart system manages the image files by automatic classification according to the patient number or the classification name of each document, based on the respective file names of the image files.

Incidentally, while sharing of information between medical institutions is required in local medical collaboration, there is a case where a collaborating medical institution uses a different electronic medical chart system. In this case, to register an image file of a patient with the electronic medical chart system of the collaborating medical institution, a user is required to select another file name rule enabling automatic classification of the image file by the electronic medical chart system of the collaborating medical institution and then change the file name of the image file, which is troublesome for the user. Thus, the conventional techniques have a problem that when providing an image file to a collaborating medical institution that makes use of a management system which uses a different file name rule, labor of a user, such as labor of changing the file name, is increased.

SUMMARY OF THE INVENTION

The present invention provides an image forming apparatus that is capable of reducing labor of a user, required when providing an image file to a collaborating medical institution that makes use of a management system which uses a different file name rule, a method of controlling the image forming apparatus, and a storage medium.

In a first aspect of the present invention, there is provided an image forming apparatus that communicates with a predetermined management system that manages image files, and a server that stores image files to be provided to a plurality of management systems including the predetermined management system, including a reading unit configured to read an original and generate an image of the original, a selection unit configured to prompt a user to select information concerning file names of the image files, at least one processor, and a memory coupled to the at least one processor, the memory having instructions that, when executed by the processor, perform the operations as: a control unit configured to perform control for converting the image of the original to an image file of a predetermined data format, a setting unit configured to set the file name of the image file to a file name at least including the information selected by the user on the selection unit, and a transmission unit configured to transmit an image file having a file name set by the setting unit, to the server, wherein the setting unit identifies a collaborating management system, out of the plurality of management systems, acquires a file name rule of the identified collaborating management system, and sets the file name of the image file according to the acquired file name rule.

In a second aspect of the present invention, there is provided a method of controlling an image forming apparatus that communicates with a predetermined management system that manages image files, and a server that stores image files to be provided to a plurality of management systems including the predetermined management system, including reading an original to generate an image of the original, performing control for converting the image of the original to an image file of a predetermined data format, prompting a user to select information concerning file names of the image files, setting the file name of the image file to a file name at least including the information selected by the user, and transmitting an image file having the set file name, to the server, wherein said setting includes identifying a collaborating management system, out of the plurality of management systems, acquiring a file name rule of the identified collaborating management system, and setting the file name of the image file according to the acquired file name rule.

According to the present invention, it is possible to reduce labor of a user, which is required when providing an image file to a collaborating medical institution that makes use of a management system which uses a different file name rule.

Further features of the present invention will become apparent from the following description of exemplary embodiments (with reference to the attached drawings).

BRIEF DESCRIPTION OF THE DRAWINGS

FIGS. 5A to 5D are diagrams each showing an example of data used to manage patient information in the present embodiment.

FIGS. 9A to 9E are diagrams each showing an example of a screen displayed on the console section appearing in FIG. 2.

FIG. 12 is a diagram showing an example of collaborating medical institution information used to manage patient information in the present embodiment.

FIG. 13 is a flowchart of a variation of the file transmission control process performed by the image forming apparatus appearing in FIG. 1.

FIG. 15 is a flowchart of another variation of the file transmission control process performed by the image forming apparatus appearing in FIG. 1.

DESCRIPTION OF THE EMBODIMENTS

The present invention will now be described in detail below with reference to the accompanying drawings showing embodiments thereof. Note that the present invention is not limited to the embodiments described below, and not all combinations of features described in the embodiments are absolutely essential to the solution according to the invention.

Figure 1:
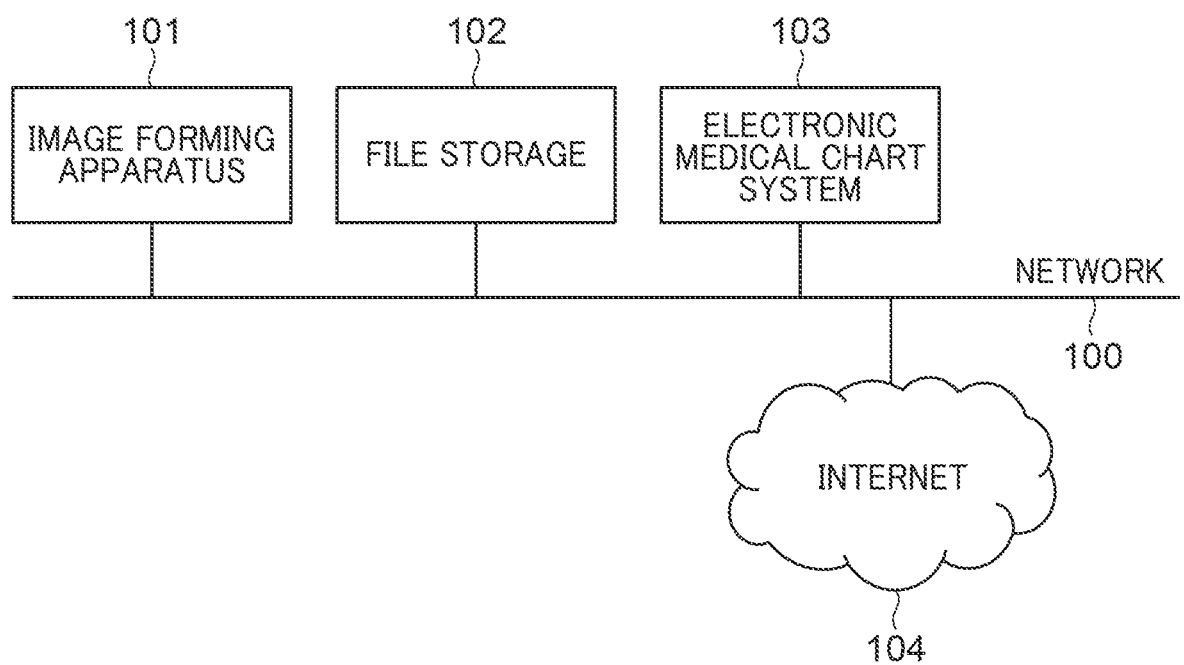
FIG. 1 is a diagram showing an example of network configuration used of an image forming apparatus according to the present embodiment.

FIG. 1 is a diagram showing an example of network configuration of an image forming apparatus 101 according to the present embodiment. The image forming apparatus 101 is implemented by a multifunction peripheral (MFP). As shown in FIG. 1, the image forming apparatus 101 is communicably connected to a file storage 102 (server) and an electronic medical chart system 103 via a network 100. The network 100 is connected to the Internet 104.

The image forming apparatus 101 reads an original and generates an image of the read original. The original is e.g. a document, such as an interview sheet or a letter of introduction from another hospital, which is submitted from a patient for receiving a medical examination. Further, the image forming apparatus 101 converts the image of the original to an image file of a predetermined data format and transmits this image file to the file storage 102. The predetermined data format is e.g. PDF, TIFF, or JPEG. The file storage 102 stores the image file received e.g. from the image forming apparatus 101. The file storage 102 provides the stored image file to a plurality of electronic medical chart systems including the electronic medical chart system 103.

The electronic medical chart system 103 registers the image file stored in the file storage 102. When registering the image file, the electronic medical chart system 103 manages the image file by performing automatic classification based on the file name of the image file. Note that although in the present embodiment, the description will be given of the configuration in which the electronic medical chart system 103 is provided separately from the file storage 102, this is not limitative, but for example, the electronic medical chart system 103 and the file storage 102 may be formed as one apparatus. Further, the image forming apparatus 101 may be configured to communicate with the file storage 102 and the electronic medical chart system 103 not via the network 100, but via the Internet 104.

Figure 2:
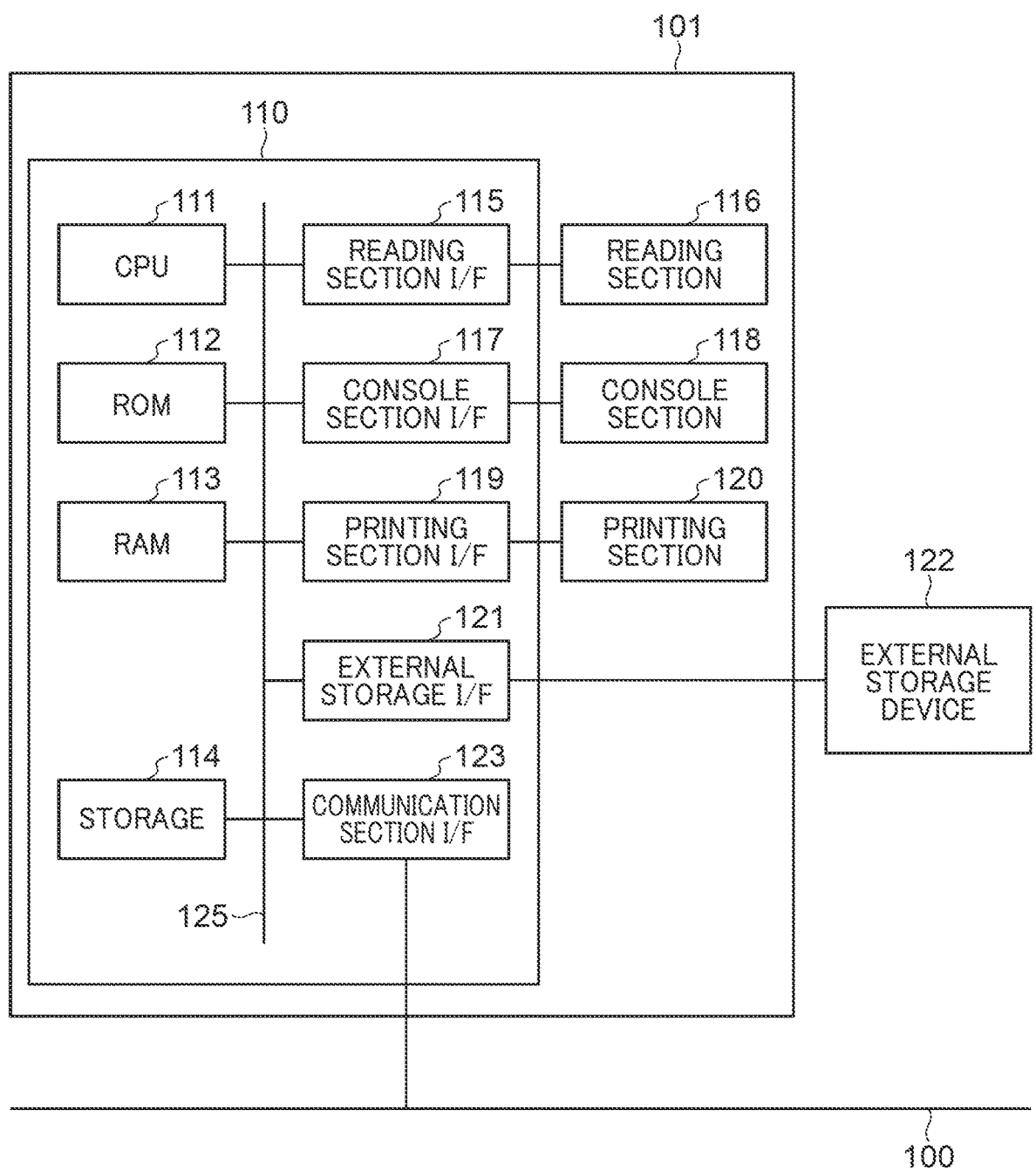
FIG. 2 is a schematic block diagram of the image forming apparatus appearing in FIG. 1.

FIG. 2 is a schematic block diagram of the image forming apparatus 101 appearing in FIG. 1. Referring to FIG. 2, the image forming apparatus 101 includes a controller 110, a reading section 116, a console section 118, and a printing section 120. The controller 110 is connected to the reading section 116, the console section 118, and the printing section 120. Further, the controller 110 includes a CPU 111, a ROM 112, a RAM 113, a storage 114, a reading section interface 115, a console section interface 117, a printing section interface 119, an external storage interface 121, and a communication section interface 123. These components are interconnected via a system bus 125.

The controller 110 controls the overall operation of the image forming apparatus 101. The CPU 111 performs a variety of controls, such as reading control and printing control, by loading programs stored in the ROM 112 or the storage 114 into the RAM 113 and executing the programs loaded in the RAM 113. The ROM 112 stores the programs executed by the CPU 111. Further, the ROM 112 stores a boot program, font data, and so forth. The RAM 113 is a main storage memory for the CPU 111. The RAM 113 is used as a work area and a temporary storage area for loading the programs stored in the ROM 112 and the storage 114. The storage 114 stores image data, print data, an address book, a variety of programs, and a variety of setting information. Note that in the present embodiment, a flash memory is assumed as the storage 114, the storage 114 is not limited to the flash memory. For example, the storage 114 may be a storage device, such as an SSD, an HDD, and an eMMC.

In the present embodiment, although the description will be given of the configuration in which the one CPU 111 executes processes, described hereinafter, using one memory (the RAM 113) by way of example, any other configuration may be employed. For example, the processes, described hereinafter, may be executed by cooperation of a plurality of CPUs, RAMs, ROMs, and storages. Further, part of the processes may be executed by using a hardware circuit, such as an ASIC and an FPGA.

The console section interface 117 connects between the console section 118 and the controller 110. The console section 118 displays information to a user and detects an input from a user. The reading section interface 115 connects between the reading section 116 and the controller 110. The reading section 116 reads an original set thereon and converts the read image to image data, such as binary data. The image data generated by the reading section 116 is transmitted to an external apparatus, stored in an external storage device 122, and printed on a recording sheet.

The printing section interface 119 connects between the printing section 120 and the controller 110. The CPU 111 transfers image data to be printed to the printing section 120 via the printing section interface 119. The printing section 120 prints an image on a recording sheet fed from a sheet feed cassette (not shown). The external storage interface 121 connects between the external storage device 122 and the controller 110. The CPU 111 stores image data in the external storage device 122 via the external storage interface 121. Although in the present embodiment, a USB interface is assumed as the external storage interface 121, and a USB memory is assumed as the external storage device 122, a storage device, such as an SD card, may be used as the external storage device 122. The communication section interface 123 connects the controller 110 to the network 100. The communication section interface 123 transmits image data to an external apparatus and receives print data from an external apparatus via the network 100.

Figure 3:
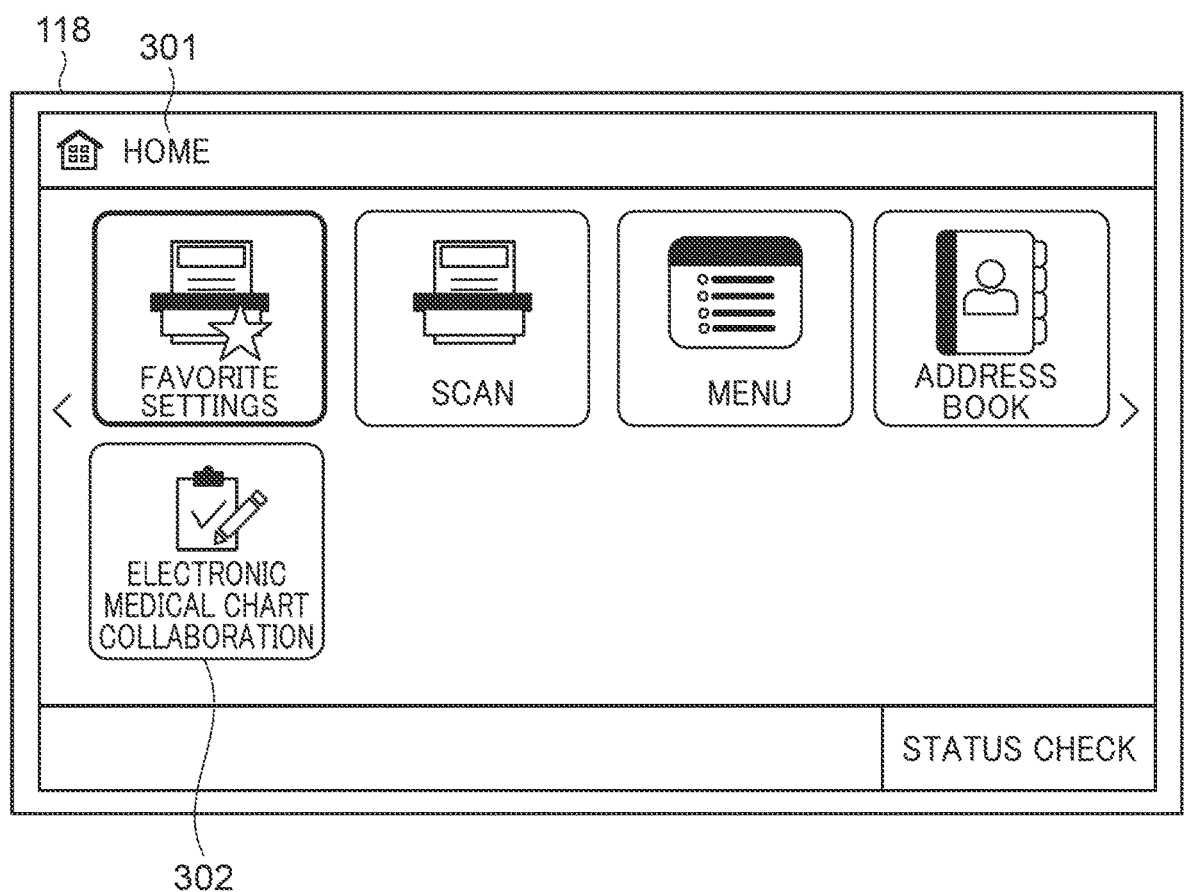
FIG. 3 is a diagram showing an example of a home screen displayed on a console section immediately after the image forming apparatus appearing in FIG. 1 is started up.

FIG. 3 is a diagram showing an example of a home screen displayed on the console section 118 immediately after the image forming apparatus 101 appearing in FIG. 1 is started up. The home screen is for instructing execution of a variety of functions of the image forming apparatus 101 and is displayed on a touch panel screen included in the console section 118. A screen name 301 is an area for displaying the name of a screen displayed on the console section 118. In FIG. 3, a name of "home" is displayed. The home screen displays a plurality of function buttons for executing the functions equipped in the image forming apparatus 101. For example, an electronic medical chart collaboration button 302 is for providing an instruction for reading a document, such as an interview sheet, a letter of introduction from another hospital, or the like, converting an image of the read document to an image file of a predetermined data format, and storing the image file in the file storage 102.

Figure 4:
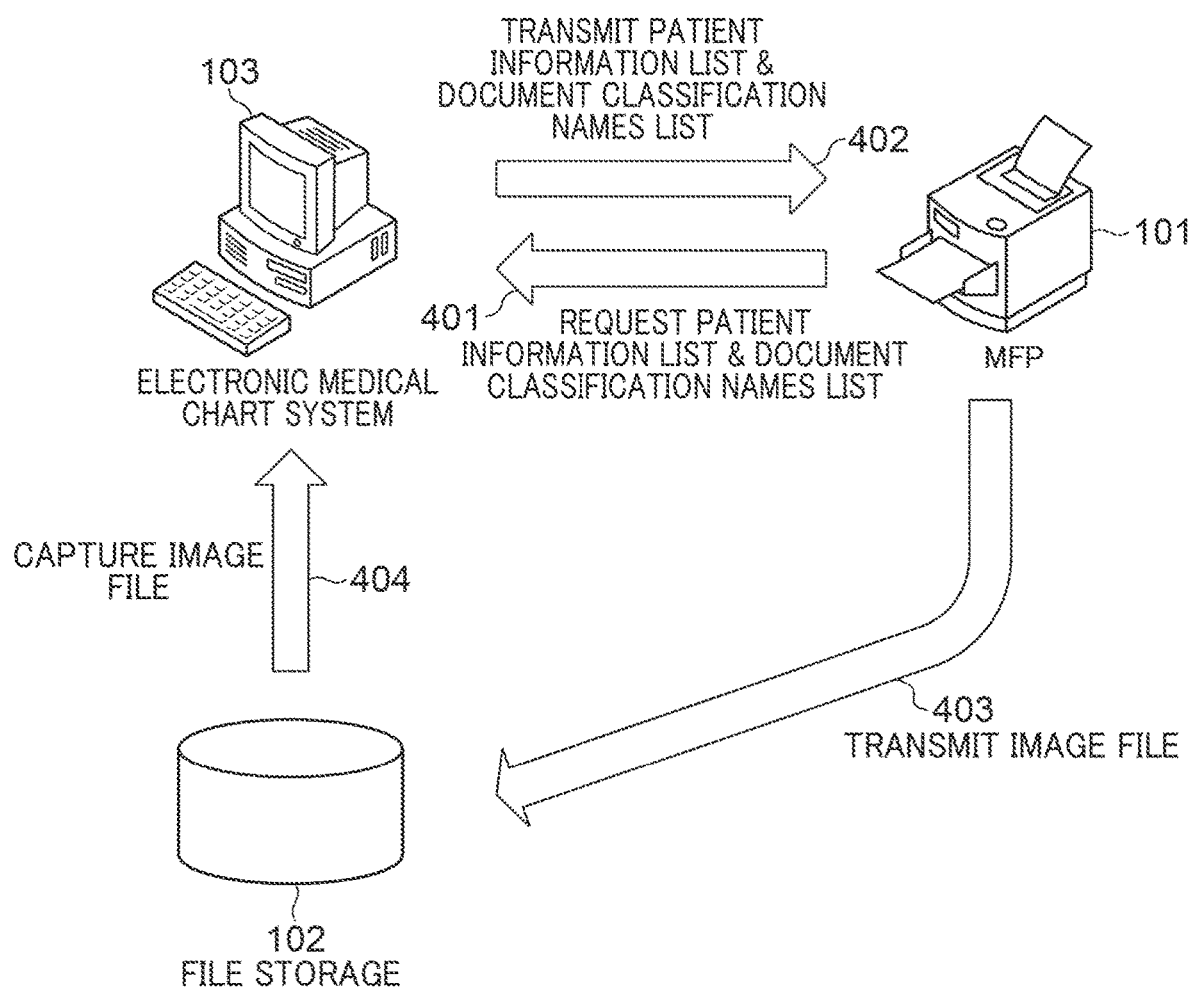
FIG. 4 is a diagram useful in explaining the outline of operations of the image forming apparatus, a file storage, and an electronic medical chart system, which are performed when an electronic medical chart collaboration button appearing in FIG. 3 is pressed.

FIG. 4 is a diagram useful in explaining the outline of operations of the image forming apparatus 101, the file storage 102, and the electronic medical chart system 103, which are performed when the electronic medical chart collaboration button 302 appearing in FIG. 3 is pressed.

When the electronic medical chart collaboration button 302 is pressed by a user, the image forming apparatus 101 reads a document set on the reading section 116, such as a letter of introduction, and generates an image file of the read document. Then, as indicated by reference numeral 401, the image forming apparatus 101 requests the electronic medical chart system 103 to transmit a list of patient information registered in a patient information database 501, described hereinafter with reference to FIG. 5A, and a list of classification names of documents registered in document classification management information 502, described hereinafter with reference to FIG. 5B.

The electronic medical chart system 103 transmits the list of patient information and the list of document classification names to the image forming apparatus 101 as indicated by reference numeral 402. The image forming apparatus 101 sets the file name of the image file and transmits the image file to the file storage 102 as indicated by reference numeral 403. The file storage 102 stores the received image file. The electronic medical chart system 103 can capture the image file stored in the file storage 102 as indicated by reference numeral 404.

FIGS. 5A to 5D are diagrams each showing an example of data used to manage the patient information in the present embodiment.

The patient information database 501 shown in FIG. 5A is for managing the patient information including a patient number for identifying a patient, a patient name, a medical department where a patient receives a medical examination, a residence address, contact information, and a state of a patient. The patient information database 501 is updated in the electronic medical chart system 103 e.g. when patient information is registered, reception of a patient is performed, hospitalization registration or payment of a bill is performed.

Figure 5B:
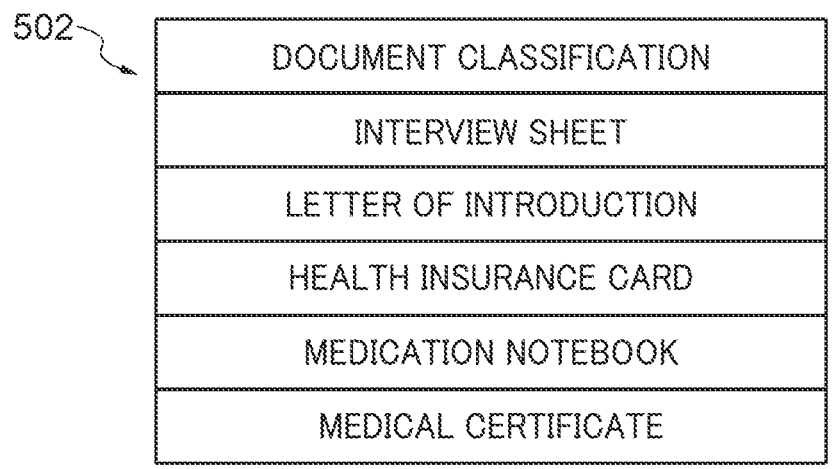

In the document classification management information 502 shown in FIG. 5B, the document classification names managed by the electronic medical chart system 103 are registered. In the document classification management information 502, for example, an interview sheet, a letter of introduction, a health insurance card, a medication notebook, and a medical certificate are registered as the document classification names.

Collaborating medical institution information 503 shown in FIG. 5C is a database for managing information concerning a collaborating medical institution, such as a name of the collaborating medical institution and information indicative of an electronic medical chart system used by the collaborating medical institution, in association with a patient number. The collaborating medical institution is a medical institution determined according to the symptoms of a patient and the like, out of a plurality of medical institutions that collaborate with a medical institution (hereinafter referred to as this hospital) in which the image forming apparatus 101 is installed and which uses the electronic medical chart system 103. Note that in a case where the plurality of medical institutions which collaborate with this hospital visited by a patient include no medical institution suitable for the symptoms of the patient, the information on collaborating medical institutions associated with the patient number of this patient does not include any collaborating medical institution names. The collaborating medical institution information 503 is updated according to a state of medical examination of the patient.

In the present embodiment, it is assumed that the patient information database 501, the document classification management information 502, and the collaborating medical institution information 503 have been stored in the electronic medical chart system 103, by way of example. The image forming apparatus 101 acquires information registered in these databases by communicating with the electronic medical chart system 103. Note that the location where the patient information database 501, the document classification management information 502, and the collaborating medical institution information 503 are stored is not limited to the electronic medical chart system 103 but may be the file storage 102 or the storage 114 of the image forming apparatus 101.

In file name rule management information 504 shown in FIG. 5D, a file name rule used by each electronic medical chart system is registered. In the present embodiment, the image forming apparatus 101 acquires the file name rule of an electronic medical chart system used by a collaborating medical institution from the electronic medical chart system 103. Alternatively, the image forming apparatus 101 directly acquires, from an electronic medical chart system used by a collaborating medical institution, the file name rule of this electronic medical chart system.

Figure 6:
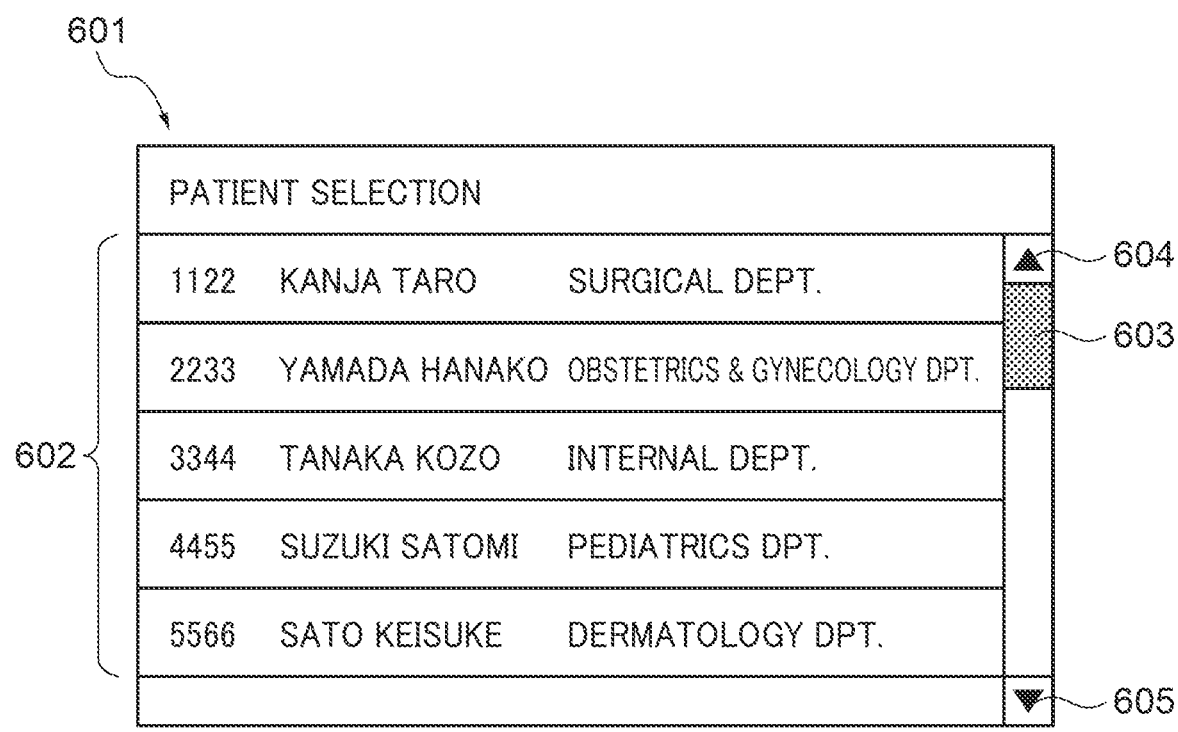
FIG. 6 is a diagram showing an example of a patient selection screen displayed on the console section appearing in FIG. 2.

FIG. 6 is a diagram showing an example of a patient selection screen 601 displayed on the console section 118 appearing in FIG. 2. This patient selection screen 601 is for prompting a user to select information indicative of the owner of the document, more specifically, information indicative of a patient possessing the document. This patient selection screen 601 is displayed on the console section 118 when a user presses the electronic medical chart collaboration button 302.

In a patient information-displaying area 602, information on patients as selection candidates are displayed in a list. Note that although in FIG. 6, a patient number, a patient name, and a medical department where a patient receives a medical examination are displayed as an example of the information on a patient, information other than these items may be displayed on the patient information-displaying area 602 as the information on the patient. The patient information-displaying area 602 is displayed based on the patient information registered in the above-described patient information database 501. The user can display other patient information items which are not displayed, by pressing and sliding a scroll bar 603 or pressing an upper scroll button 604 or a lower scroll button 605, to scroll the patient information-displaying area 602. When the user selects one patient in the patient information-displaying area 602, the patient information of the selected patient is held as the patient information associated with a scanned image. And, the screen on the console section 118 is switched to a classification selection screen 701 shown in FIG. 7.

Figure 7:
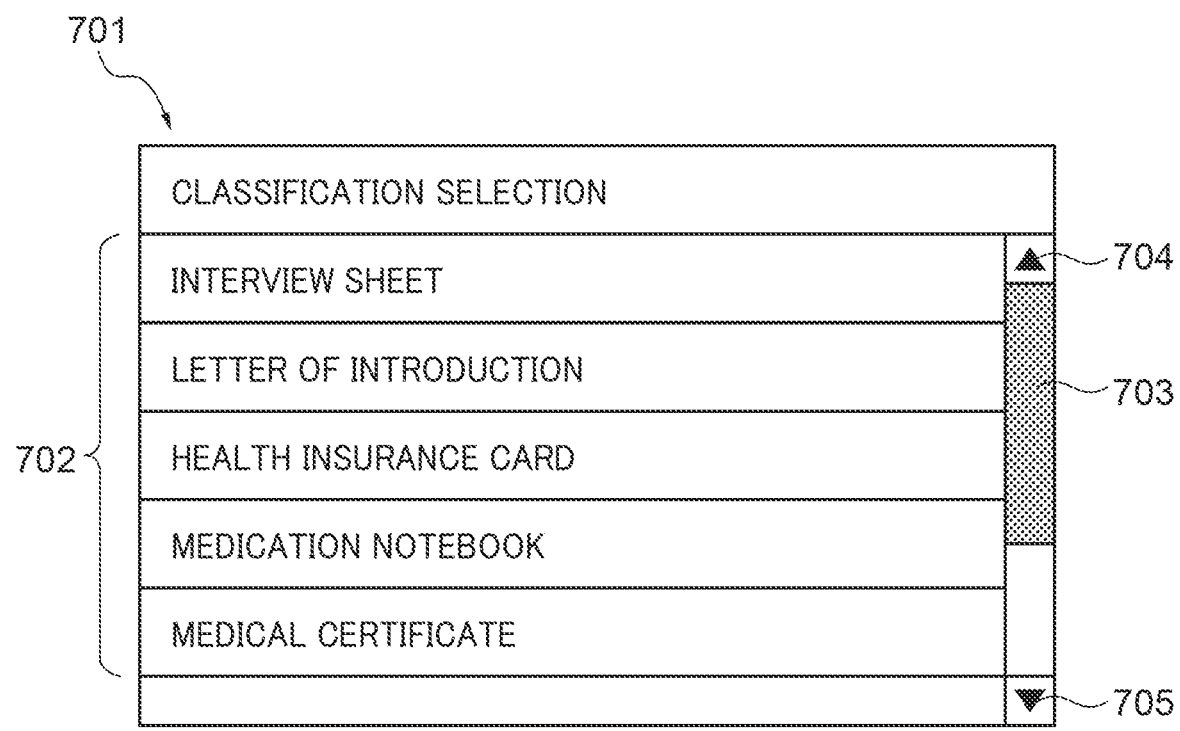
FIG. 7 is a diagram showing an example of a classification selection screen displayed on the console section appearing in FIG. 2.

FIG. 7 is a diagram showing an example of the classification selection screen 701 displayed on the console section 118 appearing in FIG. 2. This classification selection screen 701 is for selecting a document classification name to be associated with an image file generated by reading an original. In a classification information-displaying area 702, document classification names as selection candidates are displayed in a list. The classification information-displaying area 702 is displayed based on the above-described document classification management information 502. The user can display other classification names which are not displayed by pressing and sliding a scroll bar 703 or pressing an upper scroll button 704 or a lower scroll button 705 to scroll the classification information-displaying area 702. When the user selects one classification name in the classification information-displaying area 702, the selected classification name is held as the classification name associated with the image file. This classification name is used e.g. for a reading setting when reading an original and a destination setting when transmitting an image file to the file storage 102.

Figure 8:
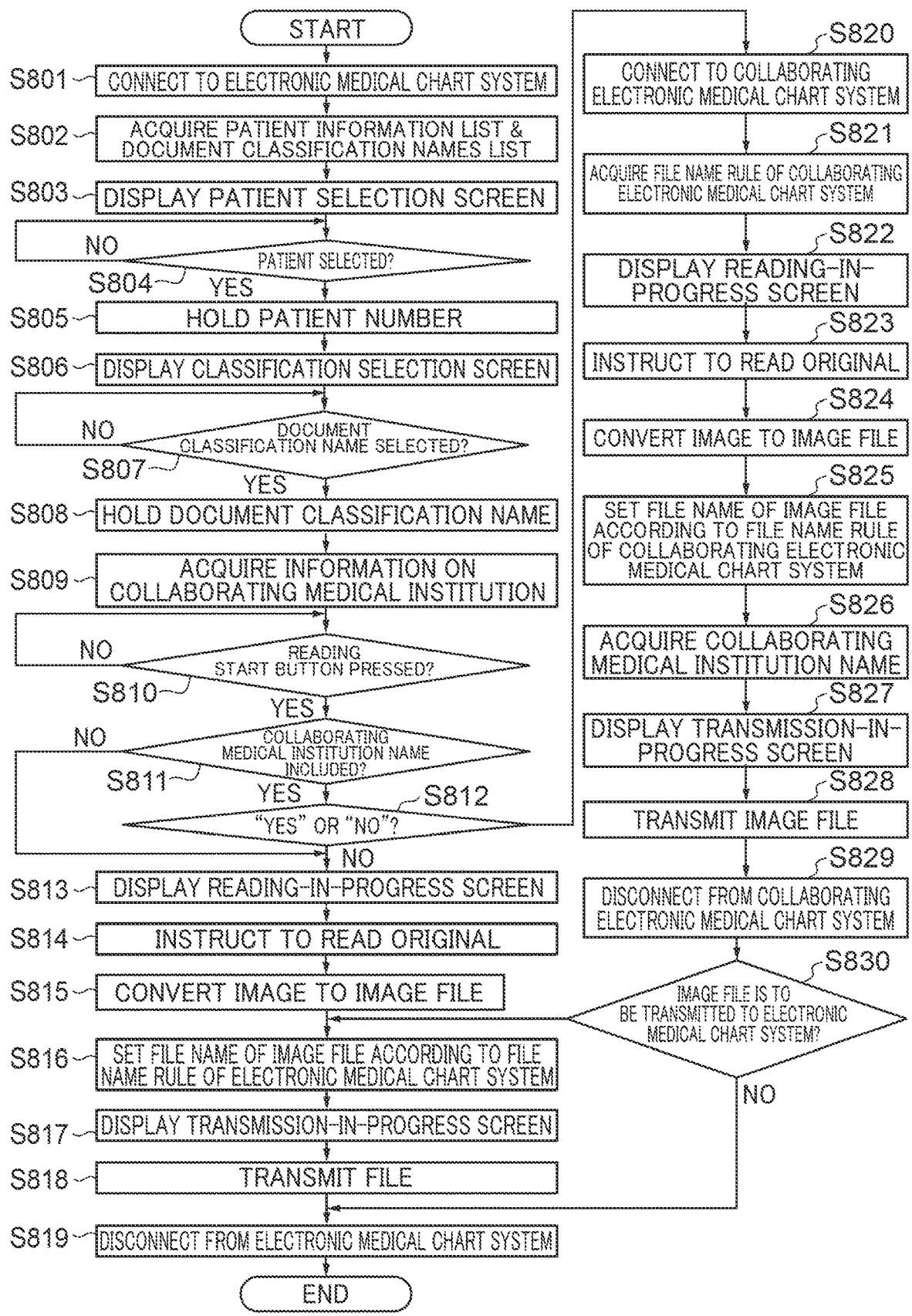
FIG. 8 is a flowchart of a file transmission control process performed by the image forming apparatus appearing in FIG. 1.

FIG. 8 is a flowchart of a file transmission control process performed by the image forming apparatus 101 appearing in FIG. 1. The file transmission control process is realized by the CPU 111 of the controller 110 that executes a program stored e.g. in the ROM 112. The file transmission control process is executed when the electronic medical chart collaboration button 302 on the home screen is pressed by a user.

Referring to FIG. 8, the controller 110 connects to the electronic medical chart system 103 (step S801). Then, the controller 110 acquires a list of patient information registered in the patient information database 501 and a list of document classification names registered in the document classification management information 502 from the electronic medical chart system 103 (step S802). Note that the timing of acquiring the list of patient information and the list of document classification names is not limited to this timing, but these lists may be acquired when the image forming apparatus 101 is started up or restored from the power-saving state. Further, the list of patient information and the list of document classification names may be regularly acquired from the electronic medical chart system 103.

Then, the controller 110 displays the above-described patient selection screen 601 shown in FIG. 6 on the console section 118 based on the list of patient information acquired in the step S802 (step S803) (operation of a display control unit). The controller 110 waits until the user selects a patient from this patient selection screen 601. When the user selects a patient from this patient selection screen 601 (YES to a step S804), the controller 110 holds the patient number of the selected patient (step S805).

Then, the controller 110 displays the above-described classification selection screen 701 shown in FIG. 7 on the console section 118 based on the list of document classification names acquired in the step S802 (step S806). Then, the controller 110 waits until the user selects a document classification name from the classification selection screen 701. When the user selects a document classification name from the classification selection screen 701 (YES to a step S807), the controller 110 holds the selected document classification name (step S808). Then, the controller 110 acquires information on a collaborating medical institution from a location where the collaborating medical institution information 503 is stored, such as the electronic medical chart system 103 (step S809). More specifically, the controller 110 acquires the information on a collaborating medical institution associated with the patient number held in the step S805 out of the plurality of information items registered in the collaborating medical institution information 503. The controller 110 waits until the user presses a reading start button (not shown) as an original reading start instruction. When the user presses the reading start button (YES to a step S810), the controller 110 determines whether or not a collaborating medical institution name is included in the information on the collaborating medical institution acquired in the step S809 (step S811). Note that as described above, in a case where the plurality of medical institutions that collaborate with this hospital visited by a patient include no medical institution suitable for the symptoms of this patient, the information on the collaborating medical institution associated with the patient number of this patient does not include the collaborating medical institution name.

If it is determined in the step S811 that a collaborating medical institution name is included in the acquired information on the collaborating medical institution, the controller 110 displays a confirmation screen shown in FIG. 9A on the console section 118. This confirmation screen is for prompting the user to confirm whether or not to transmit the image file to the electronic medical chart system of the collaborating medical institution. This confirmation screen displays the patient number held in the step S805, the name of the patient corresponding to this patient number, the document classification name acquired in the step S808, and the collaborating medical institution name included in the information on the cooperation medical institution acquired in the step S809. Further, this confirmation screen displays a "Yes" button for instructing to transmit an image file to the electronic medical chart system of the collaborating medical institution, and a "No" button for instructing not to transmit an image file to the electronic medical chart system of the collaborating medical institution. When the user selects one of the "Yes" button and the "No" button, the controller 110 determines which of the "Yes" button and the "No" button has been selected (step S812).

If it is determined in the step S812 that the selected button is the "No" button or it is determined in the step S811 that no collaborating medical institution name is included in the acquired information on the collaborating medical institution, the process proceeds to a step S813. In the step S813, the controller 110 displays a reading-in-progress screen indicating that the original is being read, as shown in FIG. 9B, on the console section 118. This reading-in-progress screen displays the patient number held in the step S805, the name of the patient corresponding to this patient number, and the document classification name acquired in the step S808.

Then, the controller 110 instructs the reading section 116 to read the original (step S814). The reading section 116 having received this reading instruction reads the set original, such as a letter of introduction, and generates an image of the read original. Then, the controller 110 converts this image to an image file of a predetermined data format (step S815). Then, the controller 110 sets a file name of the image file according to the file name rule of the electronic medical chart system 103 (step S816). There will be described, by way of example, a case where the file name rule of the electronic medical chart system 103 is a file name rule of an electronic medical chart system C in the file name rule management information 504 shown in FIG. 5D. In this case, the file name of the image file is set e.g. to "1122_letter of introduction_20211225". The number "1122" is the patient number held in the step S805. The character string "letter of introduction" is the document classification name held in the step S808. Note that although in the present embodiment, the configuration in which the document classification name held in the step S808 is directly set to the file name will be described, another character string for display, which is associated with the document classification name, may be set in place of the document classification name. The number "20211225" is a date on which the original has been read. Note that these information items may be set to tag information or header information of the image file.

Then, the controller 110 displays a transmission-in-progress screen indicating that the image file is being transmitted, as shown in FIG. 9C, on the console section 118 (step S817). This transmission-in-progress screen displays the file name and the number of pages to be transmitted of the image file. Then, the controller 110 transmits the image file to the file storage 102 via the network 100 (step S818). Then, the controller 110 disconnects from the electronic medical chart system 103 (step S819), followed by terminating the present process.

If it is determined in the step S812 that the selected button is the "Yes" button, the controller 110 connects to the electronic medical chart system of the collaborating medical institution indicated by the information on the collaborating medical institution acquired in the step S809 (step S820). In the following description, the electronic medical chart system of the collaborating medical institution is referred to as the "collaborating electronic medical chart system". Then, the controller 110 acquires the file name rule of the collaborating electronic medical chart system (step S821). Note that in the step S821, as described above, the file name rule of the collaborating electronic medical chart system may be acquired from the electronic medical chart system 103 or may be directly acquired from the collaborating electronic medical chart system. Then, the controller 110 displays a reading-in-progress screen shown in FIG. 9D, indicating that the original is being read, on the console section 118 (step S822). This reading-in-progress screen displays the patient number held in the step S805, the name of the patient corresponding to this patient number, the document classification name held in the step S808, and the collaborating medical institution name included in the information on the collaborating medical institution acquired in the step S809.

Then, the controller 110 instructs the reading section 116 to read the original (step S823). The reading section 116 having received this reading instruction reads the set original, such as a letter of introduction, and generates an image of the read original. Then, the controller 110 converts this image to an image of a predetermined data format (step S824). Then, the controller 110 sets a file name of the image file according to the file name rule of the collaborating electronic medical chart system, acquired in the step S821 (step S825). There will be described, by way of example, a case where the file name rule of the collaborating electronic medical chart system is a file name rule of an electronic medical chart system A in the file name rule management information 504 shown in FIG. 5D. In this case, the file name of the above-mentioned image file is set e.g. to "1122_letter of introduction_surgical department_20211225". The number "1122" is the patient number held in the step S805. The character string "letter of introduction" is the document classification name held in the step S807. The character string "surgical department" is information indicative of a medical department where the patient receives a medical examination, which is included in the patient information associated with the patient number held in the step S805. The number "20211225" is a date on which the original has been read. Note that these information items may be set to tag information or header information of the image file.

Then, the controller 110 acquires the collaborating medical institution name (step S826). Then, the controller 110 displays a transmission-in-progress screen indicating that the image file is being transmitted, as shown in FIG. 9E, on the console section 118 (step S827). This transmission-in-progress screen displays the file name and the number of pages to be transmitted of the image file. Further, this transmission-in-progress screen also displays the collaborating medical institution name acquired in the step S826.

Then, the controller 110 transmits the image file to the file storage 102 via the network 100 (step S828). Then, the controller 110 disconnects from the collaborating electronic medical chart system (step S829). Then, the controller 110 determines whether or not to transmit the image file to the electronic medical chart system 103 (step S830). In the step S830, for example, in a case where broadcast transmission to the collaborating electronic medical chart system and the electronic medical chart system 103 has been instructed by the user, the controller 110 determines to transmit the image file to the electronic medical chart system 103. On the other hand, in a case where broadcast transmission to the collaborating electronic medical chart system and the electronic medical chart system 103 has not been instructed by the user, the controller 110 determines not to transmit the image file to the electronic medical chart system 103.

If it is determined in the step S830 that the image file is to be transmitted to the electronic medical chart system 103, the process proceeds to the step S816. That is, in the present embodiment, in a case where broadcast transmission to the collaborating electronic medical chart system and the electronic medical chart system 103 has been instructed by the user, re-reading of the original is not performed. More specifically, the controller 110 changes the file name of the image file converted in the step S824, according to the file name rule of the electronic medical chart system 103, and then transmits this image file to the electronic medical chart system 103. With this, in a case where broadcast transmission to a plurality of electronic medical chart systems is performed, it is possible to provide the image file having a file name suitable for each electronic medical chart system, only by reading the original once.

If it is determined in the step S830 that the image file is not to be transmitted to the electronic medical chart system 103, the process proceeds to the step S819, wherein the controller 110 disconnects from the electronic medical chart system 103, followed by terminating the present process.

Figure 10:
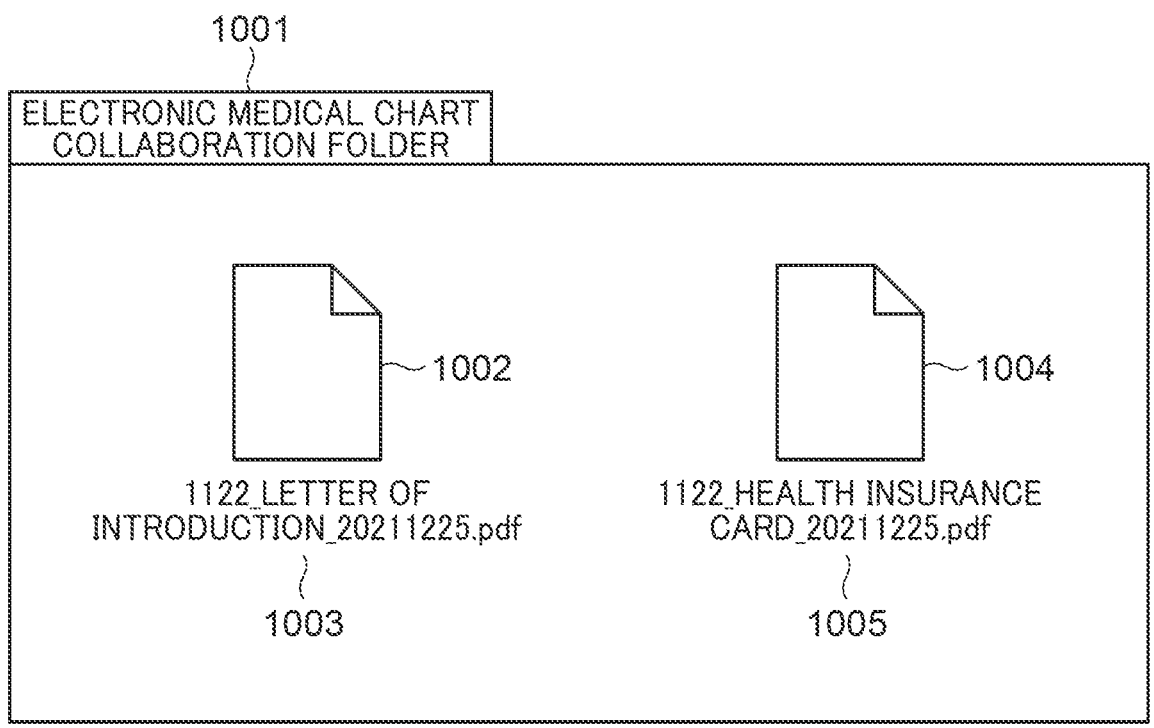
FIG. 10 is a diagram showing an example of configuration of an electronic medical chart collaboration folder of the file storage appearing in FIG. 1.

FIG. 10 is a diagram showing an example of configuration of an electronic medical chart collaboration folder 1001 of the file storage 102 appearing in FIG. 1.

Image files transmitted from the image forming apparatus 101 are stored in the electronic medical chart collaboration folder 1001 of the file storage 102. In FIG. 10, an image file 1002 and an image file 1004 have been stored. The image file 1002 is an image file generated by the reading section 116 reading an original, after the user selects "1122 Kanja Taro" on the patient selection screen 601 shown in FIG. 6 and further selects "letter of introduction" on the classification selection screen 701 shown in FIG. 7. A file name 1003 of the image file 1002 is formed as "1122_letter of introduction_20211225. pdf" according to the file name rule of an electronic medical chart system with which the image file is to be registered, e.g. the file name rule of the electronic medical chart system C. The number "1122" is the patient number selected by the user on the patient selection screen 601 shown in FIG. 6. The character string "letter of introduction" is the document classification name selected by the user on the classification selection screen 701 shown in FIG. 7. The number "20211225" is the date on which the original has been read. The character string "pdf" is an extension indicative of a file type, which is determined based on reading settings of the application.

The image file 1004 is an image file generated by the reading section 116 reading an original according to a setting of "health insurance card" changed from a setting of "letter of introduction" on the classification selection screen 701 shown in FIG. 7, after the image file 1002 has been generated. A file name 1005 of the image file 1004 is formed as "1122_health insurance card_20211225" according to the file name rule of the electronic medical chart system with which the image file is to be registered, e.g. the file name rule of the electronic medical chart system C. The file name 1005 of the image file 1004 differs from the file name 1003 of the image file 1002 only in part of the document classification name whose setting has been changed.

Figure 11:
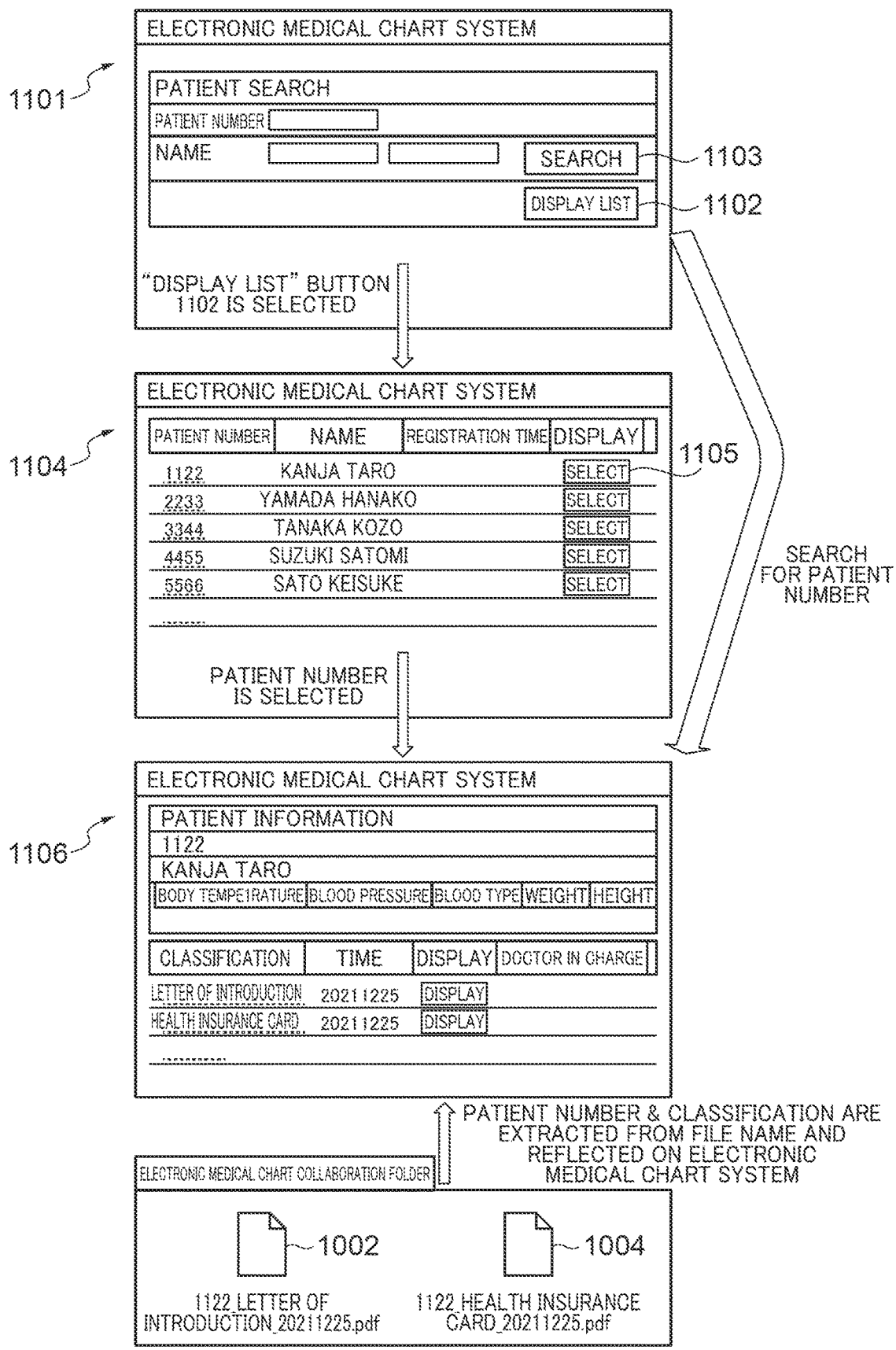
FIG. 11 is a diagram useful in explaining collaboration between the file storage and the electronic medical chart system in the present embodiment.

FIG. 11 is a diagram useful in explaining collaboration between the file storage 102 and the electronic medical chart system 103 in the present embodiment.

A display section (not shown) of the electronic medical chart system 103 displays a patient search screen 1101 for confirming patient information of a registered patient. When a "display list" button 1102 is pressed by the user on the patient search screen 1101, the screen of the display section of the electronic medical chart system 103 is changed to a list display screen 1104. The list display screen 1104 displays image files each having a file name including a patient number, out of a plurality of image files stored in the electronic medical chart collaboration folder 1001 of the file storage 102.

In a case where a "select" button 1105 is pressed by the user on the list display screen 1104, the screen of the display section of the electronic medical chart system 103 is changed to a patient information screen 1106 of a patient number associated with the "select" button 1105. In the present embodiment, also when the user inputs a patient number and presses a "search" button 1103 on the patient search screen 1101, the patient information screen 1106 of the input patient number is displayed on the display section of the electronic medical chart system 103.

The patient information screen 1106 displays a list of image files associated with the patient number associated with the "select" button 1105 or the patient number input on the patient search screen 1101, out of the plurality of image files stored in the file storage 102. For example, as shown in FIG. 11, in a case where the two image files 1002 and 1004, which have the same patient number and the different document classification names, are stored in the electronic medical chart collaboration folder 1001 of the file storage 102, information associated with the image file 1002 and information associated with the image file 1004 are displayed on the patient information screen 1106.

According to the above-described embodiment, the file name of an image file is set to a file name at least including information selected by the user on the patient selection screen 601. Further, a collaborating electronic medical chart system is identified out of a plurality of electronic medical chart systems, the file name rule of the identified collaborating electronic medical chart system is acquired, and the file name of the image file is set according to the acquired file name rule. In other words, to register the image file of the patient with the collaborating electronic medical chart system, the user is not required to select another file name rule which enables automatic classification of image files in the collaborating electronic medical chart system and change the file name of the image file. This makes it possible to reduce labor of a user when the user provides an image file to a collaborating medical institution which makes use of an electronic medical chart system which uses a different file name rule.

Further, in the above-described embodiment, the patient selection screen 601 is a screen for prompting a user to select information indicative of the owner of an original. With this, it is possible to set the file name of an image file according to the file name rule of a collaborating electronic medical chart system only by an operation of the user for selecting the information indicative of the owner of the original as information concerning the file name of the image file.

Further, in the above-described embodiment, the patient selection screen 601 is displayed on the console section 118 based on a list of patient information acquired from the electronic medical chart system 103. That is, there is no need to cause the image forming apparatus 101 to hold a list of patient information for displaying the patient selectin screen 601 in advance, as an advance preparation. This makes it possible to set the file name of an image file according to the file name rule of a collaborating electronic medical chart system without requiring the labor of the advance preparation.

In the above-described embodiment, a collaborating electronic medical chart system is identified out of a plurality of electronic medical chart systems based on information selected by the user on the patient selection screen 601. This makes it possible to identify the collaborating electronic medical chart system without forcing a user to perform an operation of setting information on a collaborating medical institution.

The present invention has been described heretofore using the above-described embodiment, but the present invention is not limited to the above-described embodiment. For example, in the file name rule, another information item included in the patient information, such as a patient name, may be included in the file name.

Further, in the above-described embodiment, items incorporated in a file name may be made changeable by an application setting.

In the above-described embodiment, not the collaborating medical institution information 503, but collaborating medical institution information 1201 shown in FIG. 12 may be used. In the collaborating medical institution information 1201, information on a collaborating medical institution, such as the name of a collaborating medical institution and information indicative of electronic medical chart system(s) used by the collaborating medical institution, is managed in association with not a patient number, but a medical department. The collaborating medical institution information 1201 is updated e.g. when the information on the collaborating medical institution is registered and edited. Similar to the collaborating medical institution information 503, the collaborating medical institution information 1201 is also stored in the electronic medical chart system 103, and the image forming apparatus 101 communicates with the electronic medical chart system 103 to acquire the information registered in the collaborating medical institution information 1201. Note that the storage location of the collaborating medical institution information 1201 is not limited to the electronic medical chart system 103 but may be the file storage 102 or the storage 114 of the image forming apparatus 101.

FIG. 13 is a flowchart of a variation of the file transmission control process performed by the image forming apparatus 101 appearing in FIG. 1. The file transmission control process in FIG. 13 is a process similar to the file transmission control process in FIG. 8, and the following description will be given, in particular, of different points from the file transmission control process in FIG. 8. The file transmission control process in FIG. 13 is also realized by the CPU 111 of the controller 110 that executes a program stored e.g. in the ROM 112. The file transmission control process in FIG. 13 is also executed when the electronic medical chart collaboration button 302 on the home screen is pressed by the user, similar to the file transmission control process in FIG. 8.

Referring to FIG. 13, the controller 110 executes steps S1301 to S1308 which are the same processing operations as the steps S801 to S808. Then, the controller 110 acquires information indicative of "medical department where a medical examination is received", which is associated with the patient number held in the step S1305 from the patient information database 501 (step S1309). Note that in the step S1309, the controller 110 acquires the above-described information from a device storing the patient information database 501, i.e. one of the electronic medical chart system 103, the file storage 102, and the storage 114 of the image forming apparatus 101. Then, the controller 110 acquires information on the collaborating medical institution, associated with the acquired "medical department where a medical examination is received" (step S1310). More specifically, the controller 110 acquires the information on the collaborating medical institution, associated with the "medical department where a medical examination is received" acquired in the step S1309, out of a plurality of information items registered in the collaborating medical institution information 1201. Note that in the step S1310, the controller 110 acquires the above-mentioned information from a device storing the collaborating medical institution information 1201, i.e. one of the electronic medical chart system 103, the file storage 102, and the storage 114 of the image forming apparatus 101. Then, the controller 110 executes steps S1311 to S 1331 which are the same processing operations as the steps S810 to S830. By using the collaborating medical institution information 1201 as described above, it is possible to easily identify, from the information indicative of a medical department where a user receives a medical examination, the collaborating medical institution of the user without making available, in advance, the collaborating medical institution information 503 in which the user and the collaborating medical institution are directly associated with each other.

Figure 14:
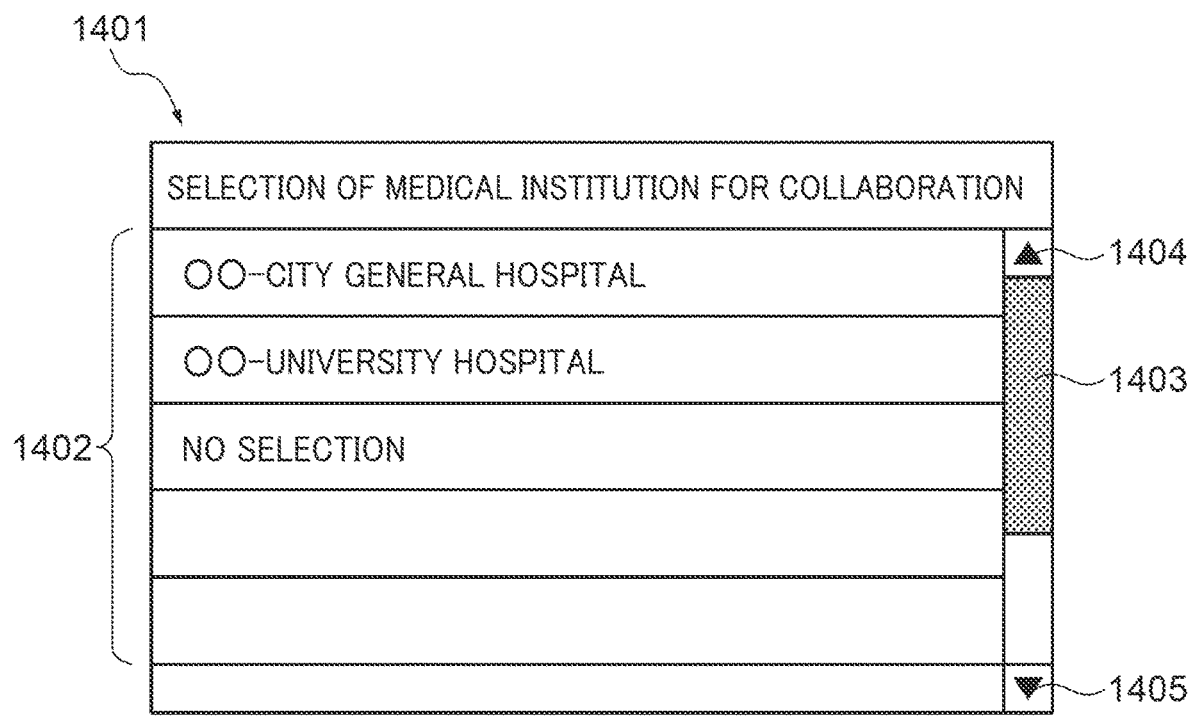
FIG. 14 is a diagram showing an example of a collaborating medical institution selection screen displayed on the console section of the image forming apparatus appearing in FIG. 1.

Further, in the above-described embodiment, the collaborating medical institution may be designated by a user. FIG. 14 is a diagram showing an example of a collaborating medical institution selection screen 1401 displayed on the console section 118 of the image forming apparatus 101 appearing in FIG. 1. The collaborating medical institution selection screen 1401 (collaborator selection screen) is for prompting a user to select information indicative of a collaborator, more specifically, a collaborating medical institution. In a collaborating medical institution-displaying area 1402, the names of the collaborating medical institutions as selection candidates are displayed in a list. The collaborating medical institution-displaying area 1402 is displayed based on list information of collaborating medical institutions, which is acquired from a device storing the information on the collaborating medical institutions of this hospital. This device is e.g. one of the electronic medical chart system 103, the file storage 102, and the storage 114 of the image forming apparatus 101. The user can display other collaborating medical institution names which are not displayed, by pressing and sliding a scroll bar 1403 or pressing an upper scroll button 1404 and a lower scroll button 1405 to scroll the collaborating medical institution-displaying area 1402.

FIG. 15 is a flowchart of another variation of the file transmission control process performed by the image forming apparatus 101 appearing in FIG. 1. The file transmission control process in FIG. 15 is also a process similar to the file transmission control process in FIG. 8, and the following description will be given, in particular, of different points from the file transmission control process in FIG. 8. Similar to the file transmission control process in FIG. 8, the file transmission control process in FIG. 15 is also realized by the CPU 111 of the controller 110 that executes a program stored e.g. in the ROM 112. Similar to the file transmission control process in FIG. 8, the file transmission control process in FIG. 15 is also executed when the electronic medical chart collaboration button 302 on the home screen is pressed by the user.

Referring to FIG. 15, the controller 110 executes steps S1501 to S1508 which are the same processing operations as the steps S801 to S808. Then, the controller 110 acquires the list information of the collaborating medical institutions (step S1509). Then, the controller 110 displays the collaborating medical institution selection screen 1401 on the console section 118 based on the acquired collaborating medical institution list information (step S1510). Then, the controller 110 waits until the user selects a collaborating medical institution from the collaborating medical institution selection screen 1401. When the user selects a collaborating medical institution from the collaborating medical institution selection screen 1401 (YES to a step S1511), the controller 110 executes steps S1512 to S1532 which are the same processing operations as the steps S810 to S830.

Thus, the collaborating electronic medical chart system is identified out of the plurality of electronic medical chart systems based on the information selected by the user on the collaborating medical institution selection screen 1401. With this, it is possible to set the file name of the image file according to the file name rule of the collaborating electronic medical chart system only by an operation of the user for selecting the collaborating medical institution.

Although in the present embodiment, the configuration using the electronic medical chart system that manages image files associated with patients has been described by way of example, this is not limitative, but any other configuration may be employed insofar as it provides an image file to a collaborating medical institution that uses a management system using a different file name rule.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-048669 filed Mar. 24, 2022, which is hereby incorporated by reference herein in its entirety.

What is claimed is:

1. An image forming apparatus that communicates with a predetermined management system that manages image files, and a server that stores image files to be provided to a plurality of management systems including the predetermined management system, comprising:
    a scanner that scans an original and generate an image of the original;
    a controller configured to,
        receive selection of a medical department from a user;
        receive selection of patient information and a classification;
        convert the image of the original to an image file of a predetermined data format,
        set a file name of the image file to a file name at least including the selected patient information and the selected classification, and
        identify, based on the selected medical department, a collaborating management system, out of the plurality of management systems, acquire a file name rule of the identified collaborating management system, and set the file name of the image file according to the acquired file name rule; and
    a communicator configured to transmit the image file having the set file name, to the server.

2. The image forming apparatus according to claim 1, further comprising a display,
    wherein the controller is configured to display on the display a selection screen, for prompting a user to select the patient information and the classification.

3. The image forming apparatus according to claim 2,
    wherein the controller is configured to display on the display the selection screen based on list information acquired from the predetermined management system.

4. The image forming apparatus according to claim 2, wherein the controller is configured to identify the collaborating management system out of the plurality of management systems, based on information selected by the user on the selection screen.

5. The image forming apparatus according to claim 1, wherein in a case where broadcast transmission to the collaborating management system and the predetermined management system is instructed, after transmitting an image file whose file name has been set according to the file name rule of the collaborating management system, to the server, the controller is configured to change the file name of the image file according to a file name rule of the predetermined management system, and the communicator is configured to transmit the image file whose file name has been changed by the controller, to the server.

6. A method of controlling an image forming apparatus that communicates with a predetermined management system that manages image files, and a server that stores image files to be provided to a plurality of management systems including the predetermined management system, comprising:
    scanning an original to generate an image of the original;
    receiving selection of a medical department from a user;
    receiving selection of patient information and a classification;
    performing control for converting the image of the original to an image file of a predetermined data format;
    setting the file name of the image file to a file name at least including the selected patient information and the selected classification;
    wherein said setting includes identifying, based on the selected medical department, a collaborating management system, out of the plurality of management systems, acquiring a file name rule of the identified collaborating management system, and setting the file name of the image file according to the acquired file name rule; and
    transmitting the image file having the set file name, to the server.

7. A non-transitory computer-readable storage medium storing a program for causing a computer to execute a method of controlling an image forming apparatus that communicates with a predetermined management system that manages image files, and a server that stores image files to be provided to a plurality of management systems including the predetermined management system,
    wherein the method comprises:
    scanning an original to generate an image of the original;
    receiving selection of a medical department from a user;
    receiving selection of patient information and a classification;
    performing control for converting the image of the original to an image file of a predetermined data format;
    setting the file name of the image file to a file name at least including the selected patient information and the selected classification;

wherein said setting includes identifying, based on the selected medical department, a collaborating management system, out of the plurality of management systems, acquiring a file name rule of the identified collaborating management system, and setting the file name of the image file according to the acquired file name rule; and transmitting the image file having the set file name, to the server.

* * * * *